US009854798B2

(12) United States Patent
Sun et al.

(10) Patent No.: US 9,854,798 B2
(45) Date of Patent: *Jan. 2, 2018

(54) WATER-SOLUBLE GRANULE FORMULATION OF 2,4-D SALT AND PREPARATION METHOD THEREOF

(71) Applicant: Shandong Weifang Rainbow Chemical Co., Ltd., Weifang, Shandong Province (CN)

(72) Inventors: Guoqing Sun, Weifang (CN); Yongsheng Hou, Weifang (CN); Yong Wu, Weifang (CN); Liwei Xu, Weifang (CN); Shuai Chen, Weifang (CN)

(73) Assignee: Shangdong Weifang Rainbow Chemical Co., Ltd., Weifang, Shandong Province (CN)

( * ) Notice: Subject to any disclaimer, the term of this patent is extended or adjusted under 35 U.S.C. 154(b) by 0 days.

This patent is subject to a terminal disclaimer.

(21) Appl. No.: 14/141,024

(22) Filed: Dec. 26, 2013

(65) Prior Publication Data

US 2014/0106973 A1 Apr. 17, 2014

Related U.S. Application Data

(63) Continuation-in-part of application No. 14/119,503, filed as application No. PCT/CN2012/000582 on May 2, 2012.

(30) Foreign Application Priority Data

Jan. 19, 2012 (CN) .......................... 2012 1 0016942

(51) Int. Cl.
*A01N 25/12* (2006.01)
*A01N 25/14* (2006.01)
*A01N 39/04* (2006.01)
*A01N 37/38* (2006.01)

(52) U.S. Cl.
CPC ............. *A01N 25/14* (2013.01); *A01N 25/12* (2013.01); *A01N 37/38* (2013.01); *A01N 39/04* (2013.01)

(58) Field of Classification Search
CPC ........ A01N 25/12; A01N 25/14; A01N 37/38; A01N 39/04
See application file for complete search history.

(56) References Cited

U.S. PATENT DOCUMENTS

| 2,694,625 | A | * | 11/1954 | Warren | ................... | A01N 39/04 504/145 |
| 5,441,923 | A | | 8/1995 | Tocker | | |
| 5,714,157 | A | * | 2/1998 | Sandell | ................... | A01N 25/14 424/405 |
| 5,883,047 | A | * | 3/1999 | Jaeger | ................... | A01N 25/26 424/405 |
| 6,022,829 | A | * | 2/2000 | Mito | ............................. | 504/134 |
| 6,387,388 | B1 | | 5/2002 | Misselbrook et al. | | |
| 6,579,831 | B1 | * | 6/2003 | Harwell | ........................ | 504/127 |
| 7,094,734 | B2 | * | 8/2006 | Ushiguchi et al. | ........... | 504/206 |
| 7,883,715 | B2 | * | 2/2011 | Abraham et al. | ............. | 424/405 |
| 2010/0248962 | A1 | * | 9/2010 | Wilczynski | .................... | 504/101 |
| 2010/0317525 | A1 | * | 12/2010 | Hidalgo | ................. | A01N 41/10 504/231 |

FOREIGN PATENT DOCUMENTS

| CN | 1040728 | | | 3/1990 | |
| CN | 1206330 | | | 1/1999 | |
| CN | 1537427 | | | 10/2004 | |
| CN | 1608465 | | | 4/2005 | |
| CN | 101326918 | | | 12/2008 | |
| CN | 101690498 | | | 4/2010 | |
| CN | 102578091 | A | * | 7/2012 | ............. A01N 39/04 |
| CN | 103081909 | A | * | 5/2013 | |
| GB | 2104780 | A | * | 3/1983 | ............. A01N 25/12 |
| JP | 2011201780 | | | 10/2011 | |

OTHER PUBLICATIONS

OTHER PUBLICATIONS

Li, Chunx, "Study of weeding non-arable weeds by 90% drop acid-Ammonium glyphosate soluble granules", Shanghai Agricultural Science and Technology, 2011, 4.
Song, Bin, "Study on Weed Control of 56% MCPA-Na SP in Wheat Field", Journal of Anhui Agricultural Sciences, Jun. 25, 2004, 32(3):466.
Yuan, Huifu et al., "Screening of the Weed Killerin the Naked Oats Field of the Hebei Northwest Region", Journal of Henan Agricultural Sciences, Nov. 15, 2009, 11:90-93.
International Search Report for PCT/CN2012/000582 dated Oct. 15, 2012.

* cited by examiner

Primary Examiner — John Pak
Assistant Examiner — Nathan W Schlientz
(74) Attorney, Agent, or Firm — Andrus Intellectual Property Law, LLP

(57) ABSTRACT

The present invention discloses a water-soluble granule formulation of 2,4-D salt, comprising components in the following weight percent: 5-80% 2,4-D salt (calculated as 2,4-D acid), and a water-soluble filler as the balance. The water-soluble granule formulation of 2,4-D salt has an outstanding control efficiency on annual or perennial Poaceae weeds and some broadleaf weeds in fields of soybean and other Fabaceae plants. The formulation is environment-friendly, and has the advantages of being free of organic solvents and dusts and being easy to measure in comparison to conventional emulsifiable formulation, wettable powder formulation and suspension formulation. The present invention also discloses the preparation method of the formulation. The production process is simple, economical and safe. The whole production process, without the use of dangerous chemicals, is easy to control and operate and has a high safety factor.

15 Claims, No Drawings

WATER-SOLUBLE GRANULE FORMULATION OF 2,4-D SALT AND PREPARATION METHOD THEREOF

CROSS-REFERENCE TO RELATED APPLICATIONS

This application is a continuation-in-part of U.S. patent application Ser. No. 14/119,503, filed Nov. 22, 2013, which is a national phase application of PCT/CN2012/000582, filed May 2, 2012, which international application claims priority to CN201210016942.X, filed Jan. 19, 2012, the contents of which are incorporated herein by reference in their entireties.

TECHNICAL FIELD

The present invention relates to a herbicide and a preparation method thereof and in particular to a water-soluble granule formulation of 2,4-D salt (i.e. water-soluble granule) and a preparation method thereof.

BACKGROUND 2,4-D, a phenoxyalkanoic acids herbicide, is a selective systemic hormone herbicide. Pure 2,4-D exists as white crystals, which has low solubility in water but is easily soluble in organic solvents such as ethanol and benzene. The amine salts and sodium salts of 2,4-D, however, are quite easily soluble in water, 2,4-D is strongly systemic. At low concentration, 2,4-D can inhibit the growth and development of the plant and cause uncontrolled growth and eventually death. 2,4-D is mainly used for post-emergence foliar treatment and has various effects on the synthesis of nucleic acids and proteins, such that the growing points of the plant stop growing, young leaves are inextensible and normal photosynthesis is inhibited. When transported to the lower parts of the plants, 2,4-D can promote uncontrolled cell division. Root tips become swollen, losing the ability of absorption. Stems and stalks become distorted and aberrant. Sieve tubes are blocked and the phloem is damaged, such that the transport of organic substances is obstructed, leading, to the death of the plant. 2,4-D herbicide has an outstanding control efficiency on annual or perennial Poaceae weeds and some broadleaf weeds in fields of soybean and other Fabaceae plants, for example, such weeds as amaranth, knotweed, lamb's-quarters, night shade, siberian cocklebur, barnyard grass, foxtail grass, digitaria sanguinalis, broomcorn millet and the like.

The main formulations of 2,4-D are emulsifiable formulation of its esters and aqueous formulation of its salts. Because the organic solvents in the emulsifiable formulation are flammable and would cause great pollution to the environment, the fraction of such formulation among herbicide formulations has been decreasing annually in recent years. Although aqueous formulation of 2,4-D salt is environment-friendly, the aqueous formulation with high concentration is very easy to crystallize at low temperatures, and the aqueous formulation with low concentration, while not easy to crystallize, will lead to increased costs in packaging and transporting, which limits the use of aqueous formulation of 2,4-D salt to some extent.

SUMMARY OF THE INVENTION

In order to overcome the disadvantages of the prior an, the present invention provides a water-soluble granule formulation of 2,4-D salt which is simple in components, friendly to the environment, and more convenient for application than other existing formulations.

The present invention further provides a preparation method of the water-soluble granule formulation whereby 2,4-D salt is readily made into water-soluble granules, with simple granulation and convenient operation.

The present invention is achieved by the following technical solution:

A water-soluble granule formulation of 2,4-D salt, comprising components in the following weight percent: 5-80% 2,4-D salt (calculated as 2,4-D acid), and a water-soluble filler which is used to make up to 100%.

Preferably, the content (by weight) of 2,4-D salt (calculated as 2,4-D acid) is 50-80%, and a water soluble filler which is used to make up to 100%.

More preferably, the content (by weight) of 2,4-D salt (calculated as 2,4-D acid) is 65-80%, and a water soluble filler which is used to make up to 100%.

Most preferably, the content (by weight) of 2,4-D salt (calculated as 2,4-D acid) is 80%, and a water soluble filler which is used to make up to 100%.

In the above-mentioned water-soluble granule formulation of 2,4-D salt, the 2,4-D salt is selected from one or more of isopropylamine salt, ethylamine salt, monomethylamine salt, dimethylamine salt, potassium salt and ammonium salt. Preferably, the 2,4-D salt is dimethylamine salt.

In the above-mentioned water-soluble granule formulation of 2,4-D salt, only a water-soluble filler is needed to prepare water-soluble granules, without the need to add any surfactant and binder. The used water-soluble filler is a water-soluble inorganic salt which is selected from one or more of sulfate, nitrate, hydrochlorate, carbonate, bicarbonate, phosphate, dibasic phosphate, monobasic phosphate, borate and silicate.

In the above-mentioned water-soluble granule formulation of 2,4-D salt, the water-soluble inorganic salts include but are not limited to ammonium sulfate, ammonium dihydrogen phosphate, disodium hydrogen phosphate, ammonium nitrate, ammonium chloride, potassium phosphate, sodium bicarbonate, sodium carbonate and anhydrous sodium sulfate.

In the above-mentioned water-soluble granule formulation of 2,4-D salt, the water-soluble inorganic salts used can be mixed in any ratio.

2,4-D salt herbicide is made into water-soluble granule formulation in the present invention, which overcomes the disadvantages existing in the aqueous formulation and makes the application of the herbicide more convenient. The water-soluble granule formulation of the present invention is simpler in components, without the need to add excipient component such as surfactant, binder and the like. Nevertheless, 2,4-D salt is hard to granulate without adding surfactant or binder. Therefore, based on the composition of the water-soluble granule formulation, the present invention provides a method suitable for preparing the formulation which allows easy granulation and convenient operation.

The preparation method of the present invention comprises: sufficiently and homogeneously mixing the 2,4-D salt and the water-soluble filler in a kneader, adding 1-10 wt % water based on the total amount of the 2,4-D salt and the water-soluble filler to perform kneading, granulating at 40-110° C. after kneading, and drying at 20-90° C.

In the above-mentioned preparation method, granulation is performed without adding any binder and surfactant, so long as it is ensured that the mixture is granulated at 40-110° C.

In comparison with the prior art, the water-soluble granule formulation of 2,4-D salt of the present invention has the following advantages:

1. The production process is simple, economical and safe. The whole production process, without the use of dangerous chemicals, is easy to control and operate and has a high safety factor.
2. The water-soluble granule formulation is environment-friendly, and has the advantages of being free of organic solvents and dusts and being easy to measure in comparison to conventional emulsifiable formulation, wettable powder formulation and suspension formulation.
3. The water-soluble granule formulation of 2,4-D salt obtained is convenient for using, which reduces the costs of packaging, storing and transporting and is suitable for large-scale popularization and application.

DETAILED DESCRIPTION OF THE PREFERRED EMBODIMENTS

Hereinafter further description will be made by incorporating examples to illustrate the present invention, which by no means should be regarded as a limitation of the present invention.

Example 1

The content by weight) of each component was: 65% 2,4-D dimethylamine salt (calculated as 2,4-D acid), and ammonium dihydrogen phosphate and disodium hydrogen phosphate which were used to make up to 100%. The components were sufficiently and homogeneously mixed in a kneader. Then 5% water was added to perform kneading followed by granulating at 55° C., drying at 82° C. Thus a water-soluble granule formulation of 65% 2,4-D dimethylamine salt (calculated as 2,4-D acid) was obtained.

Example 2

The content (by weight) of each component was: 50% 2,4-D methylamine salt (calculated as 2,4-D acid), and water-soluble inorganic salt ammonium nitrate which was used to make up to 100%. The components were sufficiently and homogeneously mixed in a kneader. Then 1% water was added to perform kneading followed by granulating at 70° C., drying at 74° C. Thus a water-soluble granule formulation of 50% methylamine salt (calculated as 2,4-D acid) was obtained.

Example 3

The content (by weight) of each component was: 5% 2,4-D ethylamine salt (calculated as 2,4-D acid), and water-soluble inorganic salt ammonium chloride which was used to make up to 100%. The components were sufficiently and homogeneously mixed in a kneader. Then 7% water was added to perform kneading followed by granulating at 40° C., drying at 65° C. Thus a water-soluble granule formulation of 5% 2,4-D ethylamine salt (calculated as 2,4-D acid) was obtained.

Example 4

The content (by weight) of each component was: 20% 2,4-D potassium salt (calculated as 2,4-D acid), and water-soluble inorganic salt potassium phosphate which was used to make up to 100%. The components were sufficiently and homogeneously mixed in a kneader. Then 10% water was added to perform kneading followed by granulating at 100° C., drying at 20° C. Thus a water-soluble granule formulation of 20% 2,4-D potassium salt (calculated as 2,4-D acid) was obtained.

Example 5

The content (by weight) of each component was: 35% 2,4-D ethylamine salt (calculated as 2,4-D acid), and water-soluble inorganic salts sodium bicarbonate and sodium carbonate which were used to make up to 100%. The components were sufficiently and homogeneously mixed in a kneader. Then 3% water was added to perform kneading followed by granulating at 95° C., drying at 43° C. Thus a water-soluble granule formulation of 35% 2,4-D ethylamine salt (calculated as 2,4-D acid) was obtained.

Example 6

The content (by weight) of each component was: 80% 2,4-D isopropylamine salt (calculated as 2,4-D acid), and water-soluble inorganic salts anhydrous sodium sulfate and disodium hydrogen phosphate which were used to make up to 100%. The components were sufficiently and homogeneously mixed in a kneader. Then 4% water was added to perform kneading followed by granulating at 85° C. drying at 90° C. Thus a water-soluble granule formulation of 80% 2,4-D isopropylamine salt (calculated as 2,4-D acid) was obtained.

Example 7

The content (by weight) of each component was: 80% 2,4-D dimethylamine salt (calculated as 2,4-D acid), and water-soluble inorganic salts anhydrous sodium sulfate and disodium hydrogen phosphate which were used to make up to 100%. The components were sufficiently and homogeneously mixed in a kneader. Then 4% water was added to perform kneading followed by granulating at 85° C., drying at 90° C. Thus a water-soluble granule formulation of 80% 2,4-D dimethylamine salt (calculated as 2,4-D acid) was obtained.

Example 8

The content (by weight) of each component was: 50% 2,4-D dimethylamine salt (calculated as 2,4-D acid), and water-soluble inorganic salts ammonium nitrate which were used to make up to 100%. The components were sufficiently and homogeneously mixed in a kneader. Then 1% water was added to perform kneading followed by granulating at 70° C., drying at 74° C. Thus a water-soluble granule formulation of 50% 2,4-D dimethylamine salt (calculated as 2,4-D acid) was obtained.

Example 9

The content (by weight) of each component was: 5% 2,4-D dimethylamine salt (calculated as 2,4-D acid), and water-soluble inorganic salts ammonium sulfate which were used to make up to 100%. The components were sufficiently and homogeneously mixed in a kneader. Then 7% water was added to perform kneading followed by granulating at 60° C., drying, at 65° C. Thus a water-soluble granule formulation of 5% 2,4-D dimethylamine salt (calculated as 2,4-D acid) was obtained.

Example 10

The content (by weight) of each component was: 75% 2,4-D dimethylamine salt (calculated as 2,4-D acid), and water-soluble inorganic salts ammonium sulfate which were used to make up to 100%. The components were sufficiently and homogeneously mixed in a kneader. Then 1% water was added to perform kneading followed by granulating at 55° C., drying at 82° C. Thus a water-soluble granule formulation of 75% 2,4-D dimethylamine salt (calculated as 2,4-D acid) was obtained.

Example 11

The content (by weight) of each component was: 55% 2,4-D dimethylamine salt (calculated as 2,4-D acid), and water-soluble inorganic salts ammonium sulfate which were used to make up to 100%. The components were sufficiently and homogeneously mixed in a kneader. Then 1% water was added to perform kneading followed by granulating at 70° C., drying at 74° C. Thus a water-soluble granule formulation of 55% 2,4-D dimethylamine salt (calculated as 2,4-D acid) was obtained.

Example 12

The content (by weight) of each component was: 80% 2,4-D dimethylamine salt (calculated as 2,4-D acid), and water-soluble inorganic salts ammonium sulfate which were used to make up to 100%. The components were sufficiently and homogeneously mixed in a kneader. Then 4% water was added to perform kneading followed by granulating at 75° C., drying at 90° C. Thus a water-soluble granule formulation of 80% 2,4-D dimethylamine salt (calculated as 2,4-D acid) was obtained.

The water-soluble granule formulations prepared in above examples are free of organic solvents and dusts, and are friendly to the environment. The water-soluble granule formulations are convenient and have remarkable effects when used to control the broadleaf weeds like lamb's-quarters and amaranth in the field, of wheat, soybean, rice, corn, and cane. Also it can be used for soil treatment after sowing before emergence in the field of corn to control some monocotyledon an dicotyledon weeds.

I. The measured properties of the water-soluber granule formulation obtained in above the examples were showed in Table 1.

TABLE 1

| Exp. | pH | Moisture content % | Foamability/mL (after 1 min) | Free phenol % | Water insoluable | Heat storage stability |
|---|---|---|---|---|---|---|
| 1 | 4.8 | 0.12 | 6 | 0.01 | Totally dissolved, No crystallization | Eligible |
| 2 | 4.6 | 0.19 | 13 | 0.02 | Totally dissolved, No crystallization | Eligible |
| 3 | 4.6 | 0.20 | 10 | 0.02 | Totally dissolved, No crystallization | Eligible |
| 4 | 5.0 | 0.25 | 11 | 0.02 | Totally dissolved, No crystallization | Eligible |
| 5 | 4.9 | 0.22 | 13 | 0.01 | Totally dissolved, No crystallization | Eligible |
| 6 | 5.1 | 0.17 | 15 | 0.02 | Totally dissolved, No crystallization | Eligible |
| 7 | 5.0 | 0.10 | 4 | 0.01 | Totally dissolved, No crystallization | Eligible |
| 8 | 4.8 | 0.15 | 5 | 0.01 | Totally dissolved, No crystallization | Eligible |
| 9 | 5.0 | 0.10 | 7 | 0.01 | Totally dissolved, No crystallization | Eligible |
| 10 | 4.8 | 0.15 | 5 | 0.01 | Totally dissolved, No crystallization | Eligible |
| 11 | 5.0 | 0.10 | 6 | 0.01 | Totally dissolved, No crystallization | Eligible |
| 12 | 4.8 | 0.15 | 5 | 0.01 | Totally dissolved, No crystallization | Eligible |

II. Weed control effects of the water-soluble granule formulation of 80% 2,4-D dimethylamine salt (calculated as 2,4-D acid) in Example 12 were studied as example.

1. Agents been Used

Test agent: the water-soluble granule formulation of 80% 2,4-D dimethylamine salt (calculated as 2,4-D acid) obtained in Example 12 of this invention.

Comparative agent: the aqueous formulation of 860 g/L 2,4-D dimethylamine salt, registered as PD20097137, produced by Shandong Weifang Rainbow Chemical Co., Ltd.

2. Field Used for Study

The study was carried out on a field of Taian Academy of Agricultural Science. No herbicide was applied on the field one year before the study. Populations of weeds in the field were stable and well-distributed. Major weeds in the field are *Amaranthus retroflexus, Chenopodium album, Sonchus brachyotus,* and *Cirsium segetum*, and some appeared sporadically are *Amaranthaceae ascendens, Portulaca oleracea*, and *Commelina communis* etc.

3. Study Methods 3.1 Dosage of the Agents.

TABLE 2

| Group | Agent | Dosage (g/mu) | Dosage of Effective components (g/ha) |
|---|---|---|---|
| 1 | Water-soluble granule formulation of 2,4-D dimethylamine salt | 50 | 720 |
| 2 | Water-soluble granule formulation of 2,4-D dimethylamine salt | 70 | 1008 |
| 3 | Water-soluble granule formulation of 2,4-D dimethylamine salt | 90 | 1296 |
| 4 | Aqueous formulation of 860 g/L 2,4-D dimethylamine salt (CK1) | 78.14 (ml) | 1008 |
| 5 | Black control (CK) | — | — |

3.2 Division of the Field Used for Study.

The field used for study was divided into 20 small test regions as shown in Table 3. Each region has an area of 40 m². The agents described above in section 3.1 were applied to the respective field according to remarks.

TABLE 3

| | | | | |
|---|---|---|---|---|
| 1 | 2 | 3 | 4 | 5 |
| 4 | 5 | 1 | 2 | 3 |
| 5 | 1 | 2 | 3 | 4 |
| 3 | 4 | 5 | 1 | 2 |

3.3 Weather Conditions on the Day when the Agents were Applied

When the agents were applied, the weather conditions were: sunny to cloudy, south wind class 1-2, mean temperature of 22.5° C. (maximum temperature of 28° C., minimum temperature of 18° C.), relative humidity 58%, and no rain. In the period of study, no atrocious climate occurred, which was advantageous for the agents to effect.

3.4 Application Method

Stem spraying method was applied, and only sprayed once. Water, in a volume be ⅓ to a volume (3 L) of a solution of the agent required for each region, i.e. about 1 L, was added into a sprayer. The agent required for each region was measured accurately and added into the sprayer. Then more water was added into to obtain a mixture with the volume required. The mixture obtained was shook to homogenous, and then was pressured and sprayed. When spraying, the solution of the agent was applied from low concentration to high concentration in sequence, so as to allow the whole weed to be applied adequately without repetition or leaking.

When the competitive agent was applied, the sprayer should be cleaned up before preparing the solution and spraying.

4. Efficacies Calculated Method

Efficacies were calculated using equation E1 or E2, $$CE(\%) = \frac{A1 - B1}{A1} \times 100 \tag{E1}$$

$$CE(\%) = \frac{A2 - B2}{A2} \times 100 \tag{E2}$$

In the equations E1 and E2, and in the hereinafter:
CE means "control effect";
SD means "significance of difference";
A1 means "Number of weeds plants in competitive field";
B1 means "Number of weeds plants in treated field";
A2 means "fresh weight of weeds plants in competitive field"; and
B2 means "fresh weight of weeds plants in treated field".

Significance of difference was analyzed by Duncan's Multiple-range Test (DMRT).

5. Results

The weeds in the field were observed everyday at a fixed position. After application, the central leaf of some weeds got chlorosis after 4~5 days, which stopped growing after 6 to 7 days, then became wilting, turned, yellow, and finally died. The weeds control status on the $15^{th}$ day and the $35^{th}$ day after application were showed in the Tables 4-6, in which, Agent 1 represented water-soluble granule formulation of 80% 2,4-D dimethylamine salt with a dosage of 720 g/ha, Agent 2 represented water-soluble granule formulation of 80% 2,4-D dimethylamine salt with a dosage of 1008 g/ha, Agent 3 represented water-soluble granule formulation of 80% 2,4-D dimethylamine salt with a dosage of 1296 g/ha, and Agent 4 represented of aqueous formulation 860 g/L 2,4-D dimethylamine salt with a dosage of 1008 g/ha.

TABLE 4

Control effect (%) calculated with the number of weeds plants on the $15^{th}$ days after application

| Agent | Amaranthus retroflexus | | Chenopodium album | | Sonchus brachyotus | | Cirsium segetum | | Other weeds | | All the weeds | |
| --- | --- | --- | --- | --- | --- | --- | --- | --- | --- | --- | --- | --- |
| | CE (%) | SD | CE (%) | SD | CE (%) | SD | CE (%) | SD | CE (%) | SD | CE (%) | SD |
| 1 | 81.42 | cC | 79.37 | cB | 76.89 | cC | 83.10 | cB | 76.90 | cC | 79.78 | cC |
| 2 | 84.50 | bB | 83.79 | bAB | 83.55 | bB | 87.32 | bAB | 81.40 | bB | 84.23 | bB |
| 3 | 87.57 | aA | 87.53 | aA | 89.27 | aA | 91.10 | aA | 86.32 | aA | 88.18 | aA |
| 4 | 83.66 | bB | 82.74 | bcAB | 81.98 | bB | 87.46 | bAB | 79.73 | bB | 93.25 | bB |

TABLE 5

Control effect (%) calculated with the number of weeds plants on the $35^{th}$ days after application

| Agent | Amaranthus retroflexus | | Chenopodium album | | Sonchus brachyotus | | Cirsium segetum | | Other weeds | | All the weeds | |
| --- | --- | --- | --- | --- | --- | --- | --- | --- | --- | --- | --- | --- |
| | CE (%) | SD | CE (%) | SD | CE (%) | SD | CE (%) | SD | CE (%) | SD | CE (%) | SD |
| 1 | 81.33 | cC | 81.77 | cC | 80.39 | bB | 82.59 | cC | 80.48 | cC | 81.53 | cC |
| 2 | 88.43 | bAB | 87.91 | bB | 85.20 | bB | 87.02 | bB | 88.58 | bB | 87.57 | bB |
| 3 | 92.34 | aA | 94.94 | aA | 92.96 | aA | 94.09 | aA | 94.11 | aA | 93.74 | aA |
| 4 | 86.71 | bB | 87.91 | bB | 85.10 | bB | 87.00 | bB | 88.34 | bcBC | 87.12 | bB |

TABLE 6

Control effect (%) calculated with weeds fresh weight on the $35^{th}$ days after application

| Agent | Amaranthus retroflexus | | Chenopodium album | | Sonchus brachyotus | | Cirsium segetum | | Other weeds | | Total weeds | |
| --- | --- | --- | --- | --- | --- | --- | --- | --- | --- | --- | --- | --- |
| | CE (%) | SD | CE (%) | SD | CE (%) | SD | CE (%) | SD | CE (%) | SD | CE (%) | SD |
| 1 | 82.65 | cC | 82.53 | cC | 84.66 | cC | 84.29 | cC | 83.56 | cB | 83.62 | cC |
| 2 | 86.19 | bB | 88.59 | bB | 90.46 | bB | 90.19 | bB | 90.49 | bB | 89.25 | bB |

TABLE 6-continued

Control effect (%) calculated with weeds fresh weight on the 35th days after application

| Agent | Amaranthus retroflexus CE (%) | SD | Chenopodium album CE (%) | SD | Sonchus brachyotus CE (%) | SD | Cirsium segetum CE (%) | SD | Other weeds CE (%) | SD | Total weeds CE (%) | SD |
|---|---|---|---|---|---|---|---|---|---|---|---|---|
| 3 | 92.46 | aA | 93.90 | aA | 95.44 | aA | 95.89 | aA | 95.46 | aA | 94.70 | aA |
| 4 | 86.30 | bB | 88.60 | bB | 90.75 | bB | 89.45 | bB | 89.99 | bB | 89.09 | bB |

Significance of difference was analyzed by Duncan's Multiple-range Test (DMRT). The results showed that the water-soluble granule formulation of 80% 2,4-D dimethylamine salt is sensitive to some weeds: *Amaranthus retroflexus, Chenopodium album, Sonchus brachyotus, Cirsium segetum, Amaranthaceae ascendens, Portulaca oleracea*, and *Commelina communis*, and the control effect increased as the increased dosage.

From the analysis of the total control effect calculated with the number of weeds plants on the 35th days after application, it can be found that the comparison differences between any two of low dosage, middle dosage, and high dosage were greatly significant. From the analysis of the total control effect calculated with weeds fresh weight on the 35th days after application, it could be found that the comparison differences between any two of low dosage, middle dosage, and high dosage were greatly significant.

From the results of the study, it could be found that the control effect of the water-soluble granule formulation of 80% 2,4-D dimethylamine salt was equivalent to that of the competitive agent with the same dosage of effective components, with no significant difference.

We claim:

1. A water-soluble granule formulation of 2,4-D salt, consisting of 20-80 wt % 2,4-D salt (calculated as 2,4-D acid), and at least one water-soluble filler as the balance to 100 wt %, wherein said at least one water-soluble filler is a water-soluble inorganic salt.

2. The water-soluble granule formulation of 2,4-D salt according to claim 1, consisting of 35-80 wt % 2,4-D salt (calculated as 2,4-D acid), and at least one water-soluble filler as the balance to 100 wt %.

3. The water-soluble granule formulation of 2,4-D salt according to claim 1, consisting of 55-80 wt % 2,4-D salt (calculated as 2,4-D acid), and at least one water-soluble filler as the balance to 100 wt %.

4. The water-soluble granule formulation of 2,4-D salt according to claim 1, consisting of 75-80 wt % 2,4-D salt (calculated as 2,4-D acid), and at least one water-soluble filler as the balance to 100 wt %.

5. The water-soluble granule formulation of 2,4-D salt according to claim 1, wherein said 2,4-D salt is selected from the group consisting of isopropylamine salt, ethylamine salt, methylamine salt, dimethylamine salt, potassium salt and ammonium salt.

6. The water-soluble granule formulation of 2,4-D salt according to claim 5, wherein said 2,4-D salt is dimethylamine salt.

7. The water-soluble granule formulation of 2,4-D salt according to claim 1, wherein said water-soluble inorganic salt is selected from the group consisting of sulfate, nitrate, hydrochlorate, carbonate, bicarbonate, phosphate, dibasic phosphate, monobasic phosphate, borate and silicate.

8. The water-soluble granule formulation of 2,4-D salt according to claim 7, wherein said water-soluble inorganic salt is selected from the group consisting of ammonium dihydrogen phosphate, disodium hydrogen phosphate, ammonium nitrate, ammonium chloride, potassium phosphate, sodium bicarbonate, sodium carbonate and anhydrous sodium sulfate.

9. The water-soluble granule formulation of 2,4-D salt according to claim 7, wherein said water-soluble inorganic salt is a mixture of water-insoluble inorganic salts.

10. A method of preparing the water-soluble granule formulation of 2,4-D salt according to claim 1, wherein said water-soluble granule formulation of 2,4-D salt is prepared by homogeneously mixing the 2,4-D salt and the at least one water-soluble filler and performing granulation at 40-110° C.

11. The method according to claim 10, wherein said preparation method comprises the following steps: homogeneously mixing the 2,4-D salt and the at least one water-soluble filler in a kneader, adding 1-10 wt % water to perform kneading, granulating at 40-110° C. after kneading, and drying at 20-90° C. to obtain the water-soluble granule formulation of 2,4-D salt.

12. The method according to claim 11, wherein the content of said each component is: 65 wt % 2,4-D dimethylamine salt (calculated as 2,4-D acid), and ammonium dihydrogen phosphate and disodium hydrogen phosphate which are used to make up to 100 wt %, the components are homogeneously mixed in a kneader, then 5 wt % water is added to perform kneading followed by granulating at 55° C., drying at 82° C., thus a water-soluble granule formulation of 65 wt % 2,4-D dimethylamine salt (calculated as 2,4-D acid) is obtained.

13. The method according to claim 11, wherein the content of said each component is: 80 wt % 2,4-D isopropylamine salt (calculated as 2,4-D acid), and water-soluble inorganic salts anhydrous sodium sulfate and disodium hydrogen phosphate which are used to make up to 100 wt %, the components are homogeneously mixed in a kneader, then 4 wt % water is added to perform kneading followed by granulating at 85° C., drying at 90° C., thus a water-soluble granule formulation of 80 wt % 2,4-D isopropylamine salt (calculated as 2,4-D acid) is obtained.

14. The method according to claim 11, wherein the content of said each component is: 80 wt % 2,4-D dimethylamine salt (calculated as 2,4-D acid), and water-soluble inorganic salts anhydrous sodium sulfate and disodium hydrogen phosphate which are used to make up to 100 wt %, the components are homogeneously mixed in a kneader, then 4 wt % water is added to perform kneading followed by granulating at 85° C., drying at 90° C., thus a water-soluble granule formulation of 80 wt % 2,4-D dimethylamine salt (calculated as 2,4-D acid) is obtained.

15. The method according to claim 11, wherein the content of said each component is: 50 wt % 2,4-D dimethylamine salt (calculated as 2,4-D acid), and water-soluble inorganic salts ammonium nitrate which are used to make up to 100 wt %, the components are homogeneously mixed in a kneader, then 1 wt % water is added to perform kneading followed by granulating at 70° C., drying at 74° C., thus a water-soluble granule formulation of 50 wt % 2,4-D dimethylamine salt (calculated as 2,4-D acid) is obtained.

* * * * *

UNITED STATES PATENT AND TRADEMARK OFFICE
CERTIFICATE OF CORRECTION

PATENT NO. : 9,854,798 B2  
APPLICATION NO. : 14/141024  
DATED : January 2, 2018  
INVENTOR(S) : Guoqing Sun et al.

Page 1 of 1

It is certified that error appears in the above-identified patent and that said Letters Patent is hereby corrected as shown below:

In the Claims  
Column 10, Line 20, Claim 9, delete "water-insoluble" and insert --water-soluble--.

Signed and Sealed this  
Eighth Day of May, 2018

Andrei Iancu  
*Director of the United States Patent and Trademark Office*